United States Patent
Eberhard et al.

(10) Patent No.: US 7,440,603 B2
(45) Date of Patent: Oct. 21, 2008

(54) METHOD AND SYSTEM FOR MULTI-ENERGY TOMOSYNTHESIS

(75) Inventors: Jeffrey Wayne Eberhard, Albany, NY (US); John Patrick Kaufhold, Schenectady, NY (US); Bernhard Erich Hermann Claus, Niskayuna (DE); Kadri Nizar Jabri, Waukesha (LB); Gopal B Avinash, New Berlin, WI (US); John Michael Sabol, Sussex (CA)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/037,730

(22) Filed: Feb. 26, 2008

(65) Prior Publication Data

US 2008/0144767 A1 Jun. 19, 2008

Related U.S. Application Data

(62) Division of application No. 10/955,269, filed on Sep. 30, 2004, now Pat. No. 7,352,885.

(51) Int. Cl.
*G06K 9/00* (2006.01)

(52) U.S. Cl. ...................................................... 382/131

(58) Field of Classification Search ................. 382/128, 382/131–132, 154, 173, 284; 378/1, 4–5, 378/19, 22
See application file for complete search history.

(56) References Cited

U.S. PATENT DOCUMENTS 6,754,298 B2   6/2004   Fessler

| | | | |
|---|---|---|---|
| 6,813,334 B2 * | 11/2004 | Koppe et al. | 378/21 |
| 7,177,390 B2 * | 2/2007 | Martin et al. | 378/25 |
| 7,356,113 B2 * | 4/2008 | Wu et al. | 378/27 |
| 2002/0141532 A1 | 10/2002 | Koppe et al. | |
| 2003/0152258 A1 | 8/2003 | Jabri et al. | |
| 2003/0215119 A1 | 11/2003 | Uppaluri et al. | |
| 2003/0215120 A1 | 11/2003 | Uppaluri et al. | |
| 2004/0066881 A1 | 4/2004 | Reddy et al. | |
| 2004/0101088 A1 | 5/2004 | Sabol et al. | |
| 2004/0101104 A1 | 5/2004 | Avinash et al. | |

FOREIGN PATENT DOCUMENTS

EP      0182529      11/2001

OTHER PUBLICATIONS

Liu, Nishimura and Makovski; "Vessel imaging using dual-energy tomosynthesis"; Medical Physics vol. 14 No. 6, Nov./Dec. 1987; pp. 950-955.

* cited by examiner

*Primary Examiner*—Daniel G Mariam
(74) *Attorney, Agent, or Firm*—Fletcher Yoder

(57) ABSTRACT

Briefly in accordance with one embodiment, the present technique provides a multi-energy tomosynthesis imaging system. The system includes an X-ray source configured to emit X-rays from multiple locations within a limited angular range relative to an imaging volume. The imaging system also includes a digital detector with an array of detector elements to generate images in response to the emitted X-rays. The imaging system further includes a detector acquisition circuitry to acquire the images from the digital detector. The imaging system may also include a processing circuitry configured to decompose plurality of images based on energy characteristics and to reconstruct the plurality of images to generate a three-dimensional multi-energy tomosynthesis image.

21 Claims, 9 Drawing Sheets

METHOD AND SYSTEM FOR MULTI-ENERGY TOMOSYNTHESIS

CROSS REFERENCE TO RELATED APPLICATIONS

This application is a divisional of U.S. patent application Ser. No. 10/955,269, (now U.S. Pat. No. 7,352,885) entitled "Method and System for Multi-Energy Tomosynthesis", filed Sep. 30, 2004, which is herein incorporated by reference in its entirety for all purposes.

BACKGROUND

The invention relates generally to the field of non-invasive imaging and more specifically to the use of multi-energy tomosynthesis imaging.

In modern healthcare facilities, imaging systems may be used in the treatment of patients, such as in the in the identification and diagnosis of diseases or other conditions. For example, X-ray based systems, such as radiographic systems, computed tomography (CT) systems, dual-energy systems, and tomosynthesis, create internal images or views of a patient based on attenuation of X-rays passing through the patient, i.e., different tissues absorb or reflect X-rays differently. Conversely, other imaging modalities, such as ultrasound, magnetic resonance imaging (MRI), and positron emission tomography (PET), may rely on other physical phenomena to create internal images or views of the patient in a non-invasive manner.

As noted above, tomosynthesis is one example of an X-ray based technique for generating internal views of the patient. In a tomosynthesis system, the X-rays are emitted at different positions relative to the patient so that three-dimensional, or depth, information is available in the acquired images. In this manner, three-dimensional images of the patient's internal regions may be obtained. However, while tomosynthesis techniques are effective in reconstructing three-dimensional images of the patient's internal regions, simultaneous presence of bone and soft tissue (or other tissue types) in the images may limit their usefulness if diagnostically interesting regions are masked or hidden by opaque tissue.

One technique used to improve the visibility of masked tissue in X-ray based imaging utilizes X-ray emissions having different energy spectra or profiles. For example, X-ray images may be acquired of a patient or portion of a patient using two different X-ray energy profiles (i.e., dual energy), such that a different set of image data is acquired for each energy profile. The different sets of image data, when processed, may be used to construct different images that characterize the density or attenuating characteristics of the imaged volume. By decomposing the acquired image data, images may also be generated which differentially reflect the composition of the imaged volume, such as bone or soft tissue in a medical context.

However, tomosynthesis imaging utilizing such dual or multi-energy techniques may still have shortcomings that reduce its usefulness. For example, a tomosynthesis image acquired using dual energy X-ray imaging may be difficult to interpret since anatomic structures, such as skeletal structures, may be removed which are useful in providing context to a reviewing radiologist. Alternatively, the image quality may be reduced by patient motion, such as respiration or cardiac motion, which may introduce motion-related artifacts into the images. The present technique may address these problems as well as others.

BRIEF DESCRIPTION

Briefly, in accordance with one embodiment, the present technique provides a multi-energy tomosynthesis imaging system. The system includes an X-ray source configured to emit X-rays from multiple locations within a limited angular range relative to an imaging volume. The imaging system also includes a digital detector with an array of detector elements to generate images in response to the emitted X-rays. The imaging system further includes a detector acquisition circuitry to acquire the images from the digital detector. The imaging system may also include a processing circuitry configured to decompose plurality of images based on energy characteristics and to reconstruct the plurality of images to generate a three-dimensional multi-energy tomosynthesis image.

In accordance with another aspect, the present technique provides a method for acquiring multi-energy tomosynthesis images. The method includes acquiring multi-energy projection images over a limited angular range and decomposing the multi-energy projection images to generate decomposed projection images. The method further includes reconstructing the decomposed projection images to generate one or more three-dimensional composition images or reconstructing the plurality of multi-energy projection images to generate one or more three-dimensional energy images. The method also includes displaying at least one of the one or more three-dimensional composition images or the three-dimensional energy images.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is generally directed towards tomosynthesis imaging techniques to generate useful images for medical and non-medical applications. As will be appreciated by those of ordinary skill in the art, the present techniques may be applied in various medical and non-medical applications, such as passenger and/or baggage screening, to provide useful three-dimensional data and context. To facilitate explanation of the present techniques, however, a medical implementation will be generally discussed herein, though it is to be understood that non-medical implementations are also within the scope of the present techniques.

Tomosynthesis imaging utilizes a limited number of projection images that are acquired over a limited angular range, generally less than 180 degrees, relative to a patient. The projection images are combined and reconstructed to generate three-dimensional images of all or part of the patient. For example, the projection images may be generated using an X-ray source moving in a plane parallel to a detector or in an arc relative to the detector and/or patient. The different views or locations from which the projections are acquired provide the desired three-dimensional information when combined and reconstructed.

Figure 1:
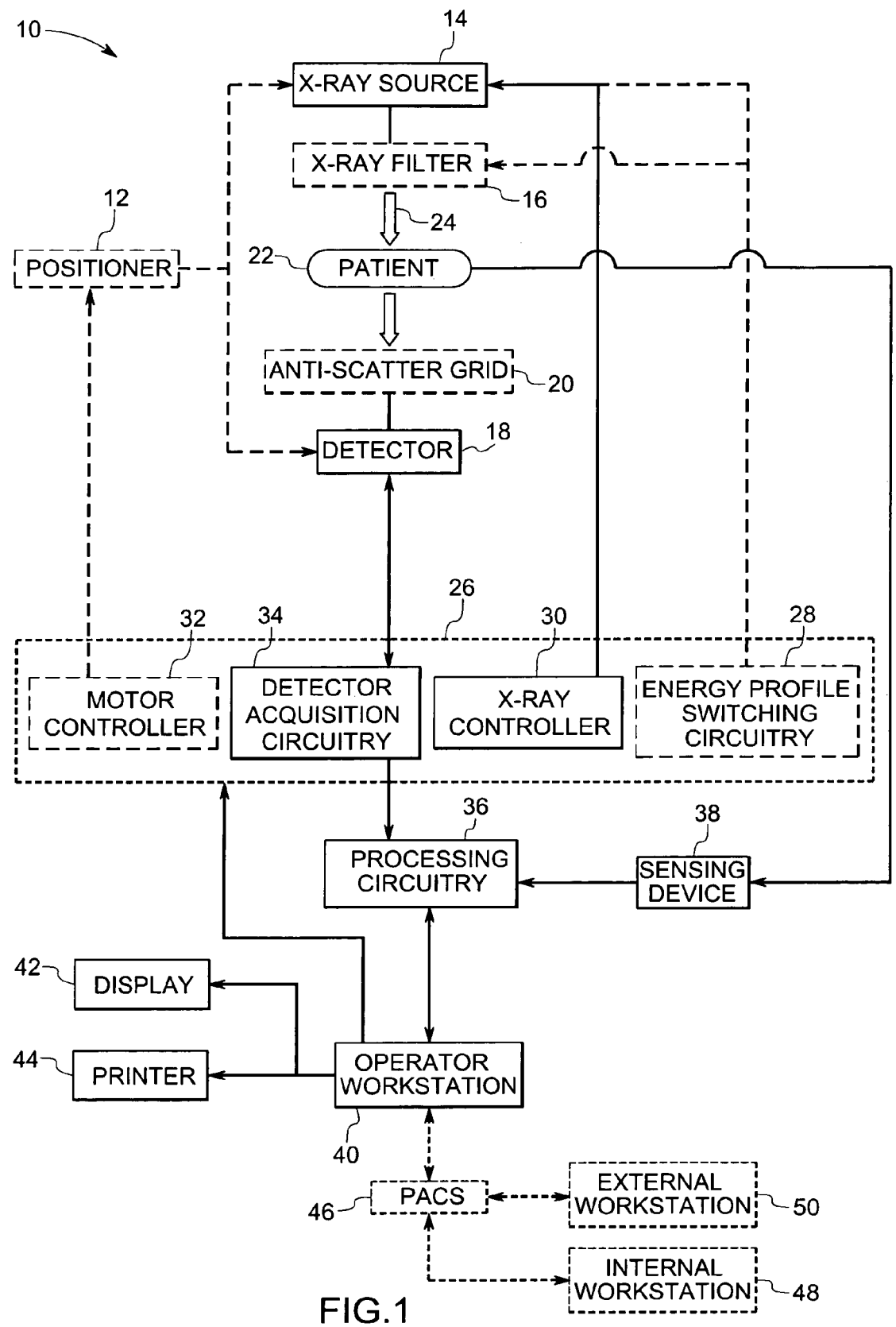
FIG. 1 depicts an exemplary embodiment of a multi-energy tomosynthesis system in accordance with the aspects of present technique.

Turning now to the drawings, and referring first to FIG. 1, an exemplary embodiment of a multi-energy tomosynthesis system 10 for use in accordance with the present technique is illustrated diagrammatically. As depicted, the tomosynthesis system 10 includes a positioner or a support 12 that supports an X-ray source 14. The support 12 may include one or more X-ray filters 16 which may be positioned between the source 14 and the imaging volume as desired. A digital detector 18, such as a flat panel detector, is generally situated across the imaging volume from the X-ray source 14 and may be stationary or may move in coordination with or independent from the X-ray source 14 and/or support 12. An anti-scatter grid 20 may also be present between the digital detector 18 and the imaging volume. When present, the anti-scatter grid 20 is typically mounted close to the digital detector 18 to reduce the incidence of scattered X-ray on the digital detector 18. In one embodiment, the anti-scatter grid may be steerable. In another embodiment, no anti-scatter grid may be present but algorithmic scatter correction may instead be performed to obtain quantitative projection images.

The X-ray source 14 is configured to emit X-rays from multiple locations, within a limited angular range, toward all or part of a patient 22 situated within an imaging volume that encompasses a region of interest in the patient 22. The X-ray source 14 may be movable in one, two or three dimensions to different locations, either manually or by automated means, such that the X-ray source 14 may change position relative to the patient 22, and/or the digital detector 18. Typically the angular range may be around but not limited to 80 degrees between the extreme positions of the X-ray source 14. In general, the angular range is typically less than 180 degrees between the extreme positions of the X-ray source 14.

Typically the X-ray source is configured to emit X-rays at one or more spectra useful for imaging the desired object or patient 22. For example, in a medical context, the X-ray source may emit a broad spectrum of X-ray radiation which may be used for patient imaging or may emit X-rays at one or more narrow spectra which are each useful for patient imaging based on the desired transmission characteristics of the X-rays. X-rays may be emitted from the X-ray source 14 at one or more locations or by one or more generators of the X-ray radiation. For example, the X-ray source 14 may be an X-ray tube configured to move to a number of locations within the angular range of the X-ray source 14 during imaging. Alternatively, the X-ray source 14 may include a number of stationary X-ray tubes at desired emission locations (i.e., an X-ray tube situated at each desired emission location) or a mixture of stationary and mobile X-ray tubes located at or capable of moving to the desired emission locations within the angular range.

While X-ray tubes are one possibility for X-ray generation by the X-ray source 14, in other embodiments the X-ray source 14 may employ other X-ray generation and emission techniques. For example, the X-ray source 14 may employ a solid-state X-ray emitter in place of the X-ray tube in the implementations described above, i.e., one or more mobile or stationary solid-state emitters. However, while X-ray tubes and solid-state X-ray emitters are two examples of X-ray generation and emission techniques which may be employed, other X-ray generation techniques or devices capable of generating X-rays having medically (or industrially) useful spectra may also be employed in conjunction with the present techniques.

The X-ray source 14, as described above, emits X-ray radiation 24 through the patient 22 towards the digital detector 18. The digital detector 18 typically includes an array of detector elements configured to generate digital signals in response to the X-ray radiation 24. In one embodiment of the present technique, the digital detector 18 does not discriminate between the energies of the different photons impacting a pixel, i.e., each pixel accumulates and represents the charge information for a variety of X-ray spectra. In such an embodiment, an X-ray filter 16 may be used to allow differentiation of X-ray energies by limiting or modifying the transmitted spectra at different times, such as for alternating X-ray emissions. The X-ray filter 16 may be made of copper, aluminum, iron, molybdenum, tin, barium, gadolinium, tungsten, lead or other suitable material. Alternatively, in another embodiment of the present technique, the X-ray source 14 may be configurable to emit X-rays at two or more spectra such that X-rays having offset spectra or energy profiles may be transmitted at different times without the use of a filter 16.

Alternatively, in yet another embodiment, the X-ray source 14 is not filtered or configured to emit at two or more spectra, however the digital detector 18 may be an energy discriminating detector, which by itself is capable of distinguishing the X-ray radiation 24 having different energy profiles or levels. For example, in one embodiment, the energy discriminating detector is used to capture both high-energy and low-energy images for a particular position of the X-ray source in one exposure. Similarly, in another embodiment, the digital detector 18 may include stacked arrays of scintillators and photodiodes in which each stack is configured to detect X-rays having different spectra or energy profiles. In this embodiment, the digital detector 18 may be used to capture high and low-energy images simultaneously.

The operation of the X-ray source 14 may be controlled by a system controller 26. For example, the system controller 26 controls the activation and operation, including collimation and timing, of the X-ray source 14 via X-ray controller 30. Furthermore, in embodiments in which the X-ray source is configured to emit X-rays at more than one energy profile, the system controller 26 may be configured to control or select the energy profile of an X-ray emission via an energy profile switching circuitry 28.

The motion of the X-ray source 14 and/or the digital detector 18 may also be controlled by the system controller 26, such as by the motor controller 32, to move independently of one another or to move in synchrony. For example, in one embodiment, the motor controller 32 may control the operation of the positioner 12, such as a C-arm, to which the X-ray source 14 and/or digital detector 18 are physically attached. In general, the positioner 12 provides the physical motion of the X-ray source 14 and/or the digital detector 18 in accordance with a pre-defined or operator selected imaging trajectory. Hence by means of the positioner 12, the system controller 26 may facilitate the acquisition of radiographic projections at various angles through the patient. Alternatively, in embodiments in which the X-ray source 14 and digital detector 18 are stationary, that is, where the X-ray source 14 comprises multiple X-ray tubes or solid state-emitters fixed at different angles relative to the detector 18, no positioner 12 is present. Alternative and hybrid configurations are possible as well, for example, in one embodiment, multiple X-ray sources 14 may be employed which move as a set (i.e., not individually). In addition, in some embodiments, the patient or the object being imaged may be moved relative to the X-ray source(s) and/or detector to generate the projection angles at different views over the limited angular range.

The system controller 26 may also control the operation and readout of the digital detector 18, such as through detector acquisition circuitry 34. In one embodiment, the digital detector 18 converts analog signals acquired in response to the X-ray radiation to digital signals and provides the same to detector acquisition circuitry 34 for further processing. Processing circuitry 36 is typically present to process and reconstruct the data read out from the digital detector 18 by the detector acquisition circuitry 34. In particular, projection data or projection images are typically generated by the detector acquisition circuitry 34 in response to the X-rays emitted by the X-ray source 14. In embodiments in which the X-rays are generated or filtered to have different spectra or energy profiles at different times, the projection images may be acquired at a particular energy profile in all defined locations and the process may be repeated for other energy profiles. Alternatively, the projection images may also be acquired for all of the energy profiles at a particular location and the process may be repeated for all defined locations. Other acquisition sequences are possible as well. However, in embodiments employing an energy discriminating detector as the digital detector 18, only one projection image is typically acquired at each location as each projection image includes the desired energy information. The projection data collected by the detector 18 may undergo pre-processing at the detector acquisition circuitry 34 and/or the processing circuitry 36. In addition, the processing circuitry 36 may reconstruct the projection data to generate one or more three-dimensional images for display.

The exemplary tomosynthesis system 10 also includes a sensing device 38 such as, but not limited to, a cardiac motion sensor or a respiratory motion sensor. The sensing device 38 can be connected to a patient 22 to monitor activity associated with the internal or external motion within the imaging volume, such as electrical activity, displacement, acceleration, strain, velocity, pressure and sound associated with the motion of one or more organs within the imaging volume. The data obtained by the sensing device 38 may also be acquired and processed by the processing circuitry 36.

The processing circuitry 36 may decompose the projection images based on energy characteristics such that different energy characteristics are associated with different material types. The processing circuitry 36 may further reconstruct the projection images to generate three-dimensional tomosynthesis images. As discussed below, the steps of reconstruction and decomposition may be performed in either order, but, in general, when both steps are performed, composition three-dimensional tomosynthesis images, which represent different material or tissue types, are generated. For example, the composition tomosynthesis images may include a soft tissue tomosynthesis image, a bone-tomosynthesis image, and/or a contrast image. Conversely, if the processing circuitry reconstructs the acquired projection data without also decomposing the projection data, energy tomosynthesis images, such as a low-energy tomosynthesis image, an intermediate-energy image and a high-energy tomosynthesis image may be generated. These energy tomosynthesis images depict the attenuation of X-rays at the respective energy profile by the patient 22 or object in the imaging volume. In a medical context, the various tomosynthesis images reveal an internal region of interest of the patient 22, which may be used for further diagnosis. The processing circuitry 36 may also include memory circuitry to store the processed and to be processed data. The memory circuitry may also store processing parameters, and/or computer programs.

The processing circuitry 36 may be connected to an operator workstation 40. The images generated by the processing circuitry 36 may be sent to the operator workstation 40 for display, such as on the display 42. The processing circuitry 36 may be configured to receive commands or processing parameters related to the processing or images or image data from the operator workstation 40, which may include input devices such as a keyboard, a mouse, and other user interaction devices (not shown). The operator workstation 40 may also be connected to the system controller 26 to allow an operator to provide commands and scanning parameters related to the operation of the X-ray source 14 and/or the detector 18 to the system controller 26. Hence an operator may control the operation of all or part of the system 10 via the operator workstation 40.

The operator workstation 40 is typically connected to a display 42 and/or to a printer 44 capable of rendering the tomosynthesis images generated by the processing circuitry 36. Display and/or printer circuitry within the operator workstation 40 typically provides the tomosynthesis images to the respective display 42 or printer 44 for rendering. Further the operator workstation 40 may also be connected to a picture archiving system (PACS) 46, which may in turn be connected to an internal workstation 48 and/or an external workstation 50 through networks so that people at different locations may gain access to the tomosynthesis images and/or image data. Similarly, the operator workstation 40 may access images or data accessible via the PACS 46 for processing by the processing circuitry 36 and/or rendition on the display 42 or printer 44.

Figure 2:
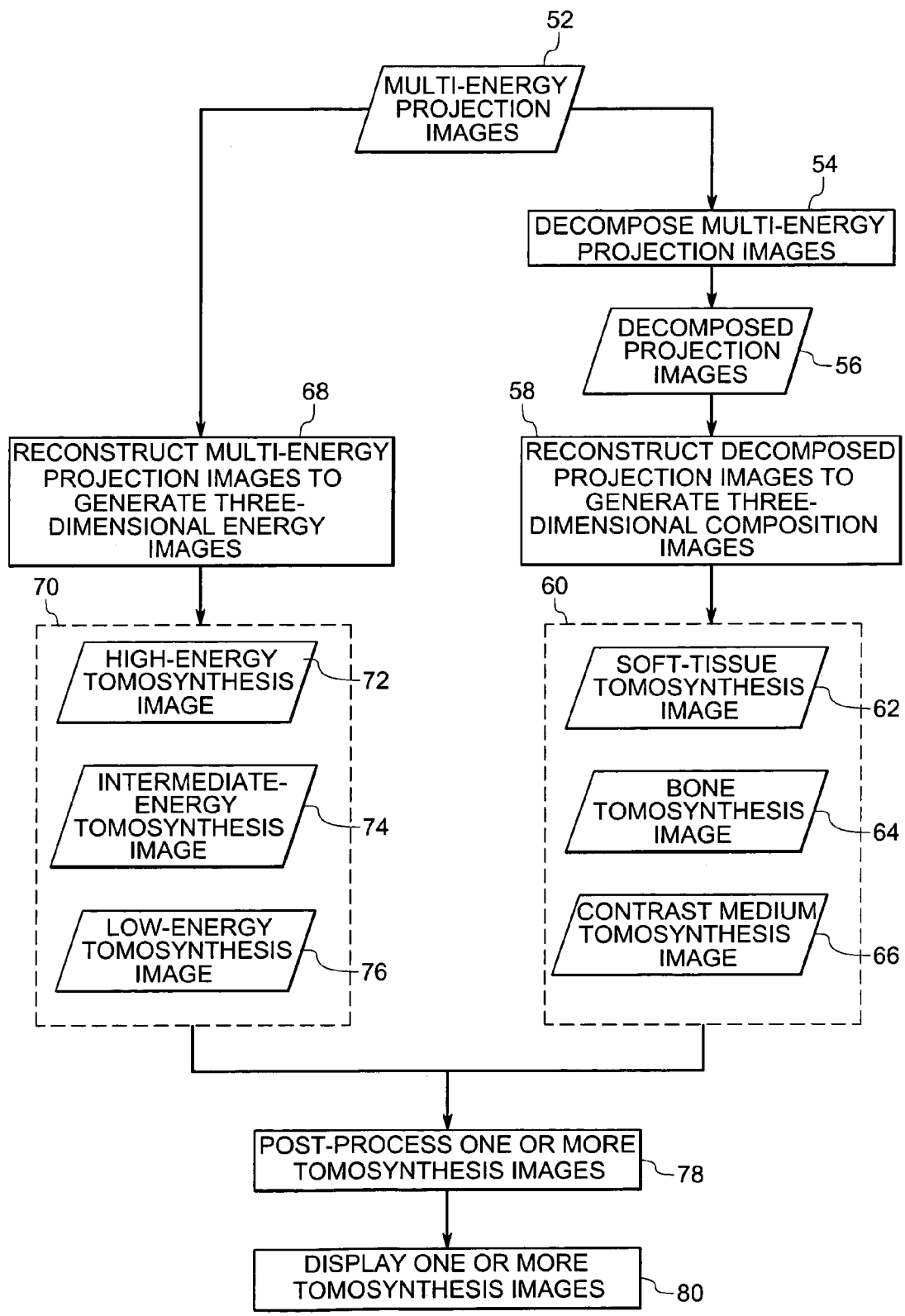
FIG. 2 is a flowchart illustrating exemplary process steps for acquiring and reconstructing multi-energy tomosynthesis images in accordance with aspects of present technique.

Keeping in mind the system of FIG. 1, FIG. 2 illustrates exemplary process steps for acquiring, reconstructing, and displaying multi-energy tomosynthesis images in accordance with aspects of present technique. The exemplary method represented includes acquiring multi-energy projection images 52 for each energy profile (i.e., X-ray spectrum) and location (i.e., emission point) of interest. For example, as described above, the projection images may be acquired at a particular energy profile in all the defined locations and the process may be repeated for the remaining energy profiles. Alternatively, the projection images may also be acquired for all of the energy profiles at a particular defined location and the process may be repeated for the remaining locations.

As described above, the acquired multi-energy projection images 52 may be decomposed to differentiate the image data based on material densities or composition (such as the depicted first and second tissue type), shown in step 54. The projection images may be decomposed using log-subtraction, base material decomposition methods to name but few methods. The decomposition process 54 generates a number of decomposed projection images 56. As will be appreciated by those skilled in the art, decomposing the projection images at step 54 may be based on the energy characteristics of the acquired projection data, such that different energy characteristics are associated with different material types. The decomposed projection images 56 are then reconstructed to generate three-dimensional composition images 60 of one or more of the respective material types, as depicted at step 58. For example, reconstruction at step 58 may be performed using reconstruction algorithms such as filtered back-projection, algebraic reconstruction, techniques, shift and add, Fourier reconstruction, objective function-based reconstruction to name but few algorithms. In one embodiment, these three-dimensional composition images 60 may include soft-tissue tomosynthesis images 62, bone-tomosynthesis images 64, and contrast medium tomosynthesis image 66. Further, three-dimensional energy images 70 may also be generated by reconstructing, without decomposing, the multi-energy projection images 52 at step 68. The three-dimensional energy images 70 may include high-energy tomosynthesis images 72, intermediate-energy tomosynthesis images 74 and low-energy tomosynthesis images 76. The three-dimensional images described above may provide quantitative data, such as density and other characteristics of the material type.

The one or more tomosynthesis images as described above may undergo post-processing at step 78 to minimize or avoid artifacts or to otherwise modify or enhance the images. The three-dimensional tomosynthesis images may then be displayed or rendered by the operator workstation 40 onto the respective display 42 or printer 44 at step 80.

For example, at step 80 the display circuitry may display one or more of the three-dimensional images by allowing an operator to toggle between two or more of the images. In another embodiment, the display circuitry is configured to concurrently or alternately display two or more three-dimensional images on one or more displays 42. In other embodiments, the display circuitry also is configured to display structural features of a first three-dimensional image, such as a contrast medium tomosynthesis image 66, superimposed on a second three-dimensional image, such as a soft-tissue tomosynthesis image 62. In a further embodiment, the display circuitry is configured to display a combination of one or more three-dimensional images. In another embodiment, the display circuitry is configured to display two or more of the three-dimensional images using a synchronized cine visualization technique.

Figure 3:
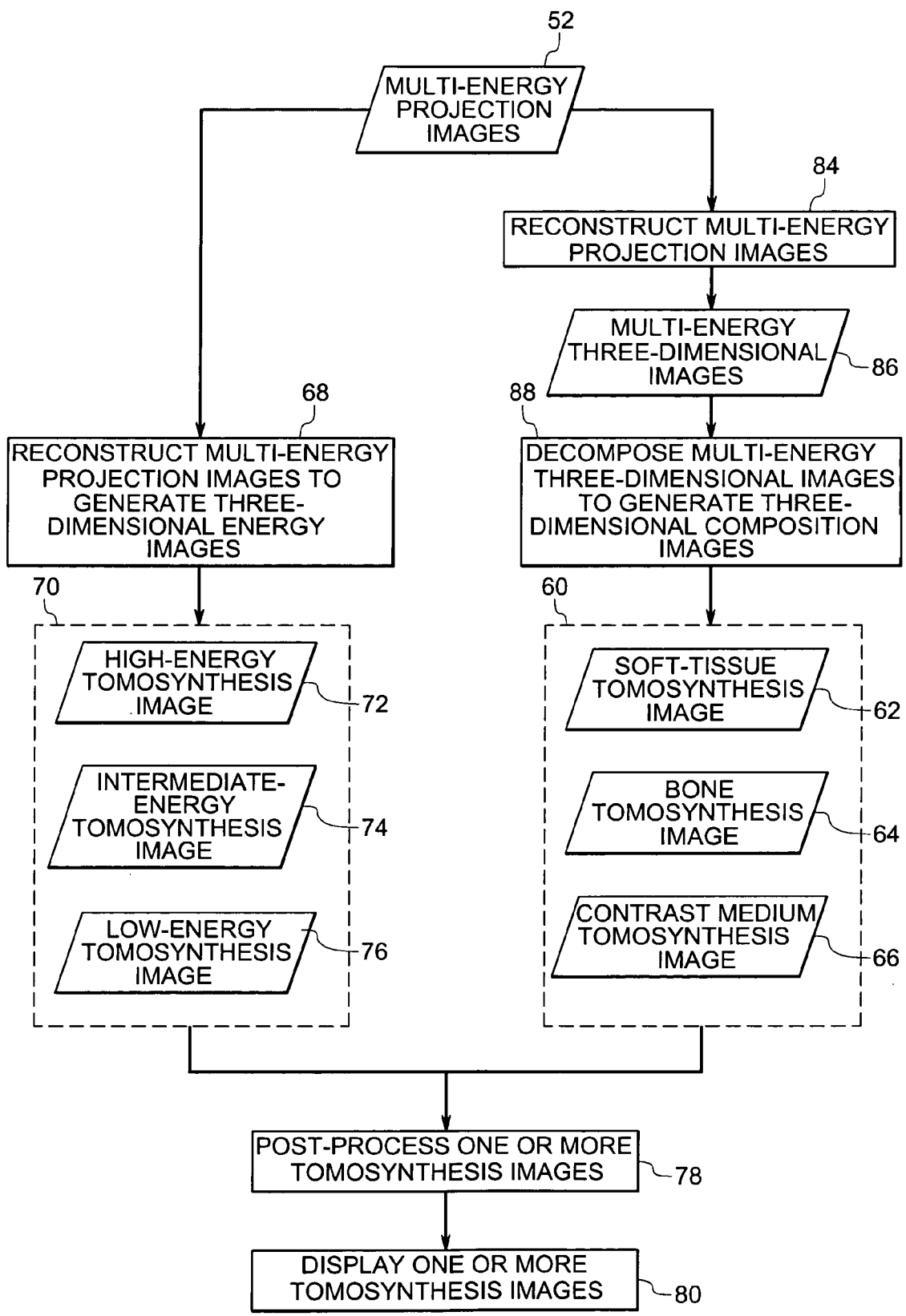
FIG. 3 is a flowchart illustrating exemplary process steps for acquiring and reconstructing multi-energy tomosynthesis images in accordance with another embodiment of present technique.

Alternatively, the process for acquiring, reconstructing, and displaying multi-energy tomosynthesis images may be performed such that reconstruction precedes decomposition in generating the composition three-dimensional images 70, as depicted in FIG. 3. In this embodiment, the multi-energy projection images 52 are reconstructed at step 84 to generate multi-energy three-dimensional images 70. As depicted in FIG. 3, in the absence of a subsequent decomposition step 88, the reconstructed three-dimensional energy images 70 are equivalent to those described with regard to FIG. 2, i.e., high-energy tomosynthesis images 72, intermediate-energy tomosynthesis images 74, and high-energy tomosynthesis images 76. However, if the reconstructed three-dimensional energy images 70 are decomposed at step 88, three-dimensional composition images 60 are generated. As described above, these three-dimensional composition images 60 may include soft-tissue tomosynthesis images 62, bone-tomosynthesis images 64, and contrast medium tomosynthesis image 66. These tomosynthesis images may then undergo post processing at step 78 and be displayed and visualized at step 80.

In one embodiment, the multi-energy projection images are acquired for a limited number of locations or emission points of the X-ray source 14 and single energy projection images (or images acquired at fewer energy profiles than in the first number of locations) are acquired for other locations or emission points. The multi-energy projection images may then be processed in accordance with the techniques of FIGS. 2 and 3 to generate composition tomosynthesis images 60 relying on the composition information derived from the limited number of multi-energy projection images. The composition tomosynthesis images 60 may then be projected over the single energy images and subtracted to generate images of other structures such as soft tissue. In one example, dual-energy images are acquired for a first subset of the emission points of the X-ray source, and these images are then used to reconstruct a three-dimensional bone tomosynthesis image. Using information from this three-dimensional bone tomosynthesis image, the differential contribution of the bone in the other collected projection images (corresponding to a second subset of x-ray emission points) can be determined and removed, e.g., by re-projecting the bone tomosynthesis image, and subtracting the reprojected images from the collected projection images. The resulting images (corresponding to the second subset of X-ray emission points) show only soft tissue information, and can thus be used in combination with the soft-tissue images corresponding to the first subset of x-ray emission points to reconstruct a high-quality soft tissue tomosynthesis image.

Figure 4:
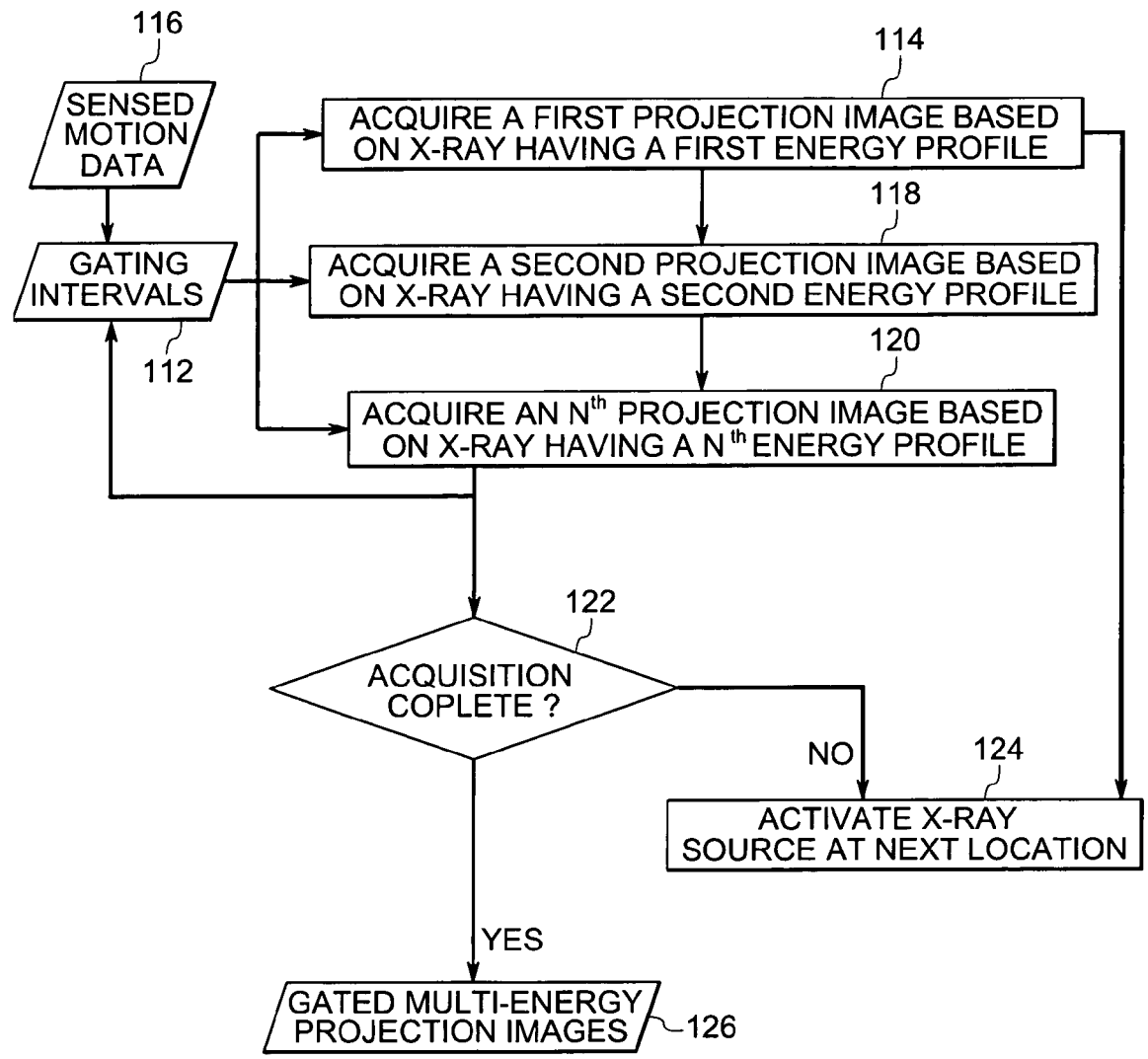
FIG. 4 is a flowchart illustrating exemplary process steps for acquiring gated multi-energy tomosynthesis images based on prospective gating in accordance with aspects of present technique.

In some embodiments it may be desirable to limit projection image acquisition to desired periods or phases corresponding to a cyclic or repeated motion, such as a heartbeat or respiration. FIG. 4 is a flowchart illustrating one exemplary embodiment for acquiring gated multi-energy tomosynthesis images using prospective gating. The exemplary process includes acquiring a first projection image based on X-rays having a first energy profile, as depicted at step 114, and a second projection image based on X-rays having a second energy profile, as depicted at step 118. Furthermore, as will be appreciated by those of ordinary skill in the art, additional projection image acquisitions may occur for additional X-ray energy profiles, as depicted at step 120.

The projection image acquisitions of steps 114, 118, and 120 are based on one or more respective gating intervals 112. The gating interval 112 may be determined based upon a period of interest, such as a period of minimum cardiac or respiratory motion, and is based on sensed motion data 116 in one embodiment. In this embodiment, the sensed motion data 116 includes data derived from the other devices, such as the sensing device 38, that record patient or organ motion in the imaged region during the image acquisition process. In another embodiment, the gating intervals 112 may be derived from the acquired projection data, such as from an initial or preliminary set of projection images, from which the cyclic or repeated motion of the organs within the field of view is determined.

A determination is made whether the process of acquiring projection images at all defined or desired locations is completed, as in step 122. If acquisitions have not occurred at all desired locations, the X-ray source is moved or activated at the next location, as depicted at step 124, and projection images are acquired based on the gating interval 112. Alternatively, the projection images may be acquired in a different order or sequence. Once image acquisition is complete, as determined at step 122, the resulting gated multi-energy projection images 126 may be processed in accordance with the preceding discussion to generate one or more desired tomosynthesis images.

Figure 5:
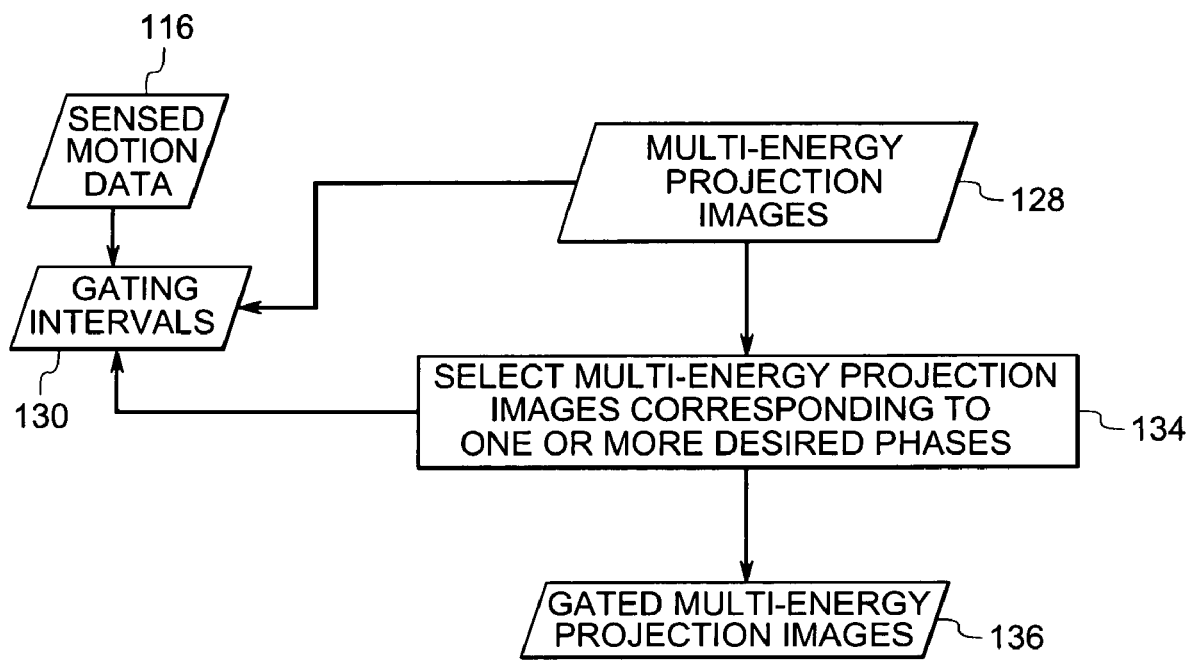
FIG. 5 is a flowchart illustrating exemplary process steps for acquiring gated multi-energy tomosynthesis images based on retrospective gating in accordance with aspects of present technique.

In another embodiment, as depicted in FIG. 5, retrospective gating may be employed to generate a set of gated multi-energy projection images. For example, in this embodiment, an extended set of multi-energy projection images 128, such as may be acquired using a volumetric imaging system rotated less than 180 degrees about a patient, may be retrospectively gated such that only those projection images corresponding to a desired phase or phases are processed. For example, as depicted at step 134, those multi-energy projection images corresponding to one or more desired phases of motion may be selected from the extended set of multi-energy projection images 128 based upon one or more gating intervals 130. The gating intervals 130 may be derived from sensed motion data 116 as discussed above, or from motion data derived from the projection images of the extended set of multi-energy projection images 128. The gated multi-energy projection images 136 thereby selected may be processed in accordance with the preceding discussion to generate one or more desired tomosynthesis images. In one embodiment, the set of gated multi-energy projection images 136 may be used to generate four-dimensional data sets for viewing which include temporal information. In particular, in this embodiment, the extended set of multi-energy projection images 128 and the selection of multiple phases of interest, as reflected in the gating intervals 130, may allow for the selection of projection images at more than one phase of interest at step 134.

While the preceding discussion addresses the minimization of image differences attributable to the timing via gating techniques, spatial differences may also be present in the acquired projection images due to motion not attributable to cyclic or repetitive behaviors. These spatial differences may be addressed at different times by image registration. As will be appreciated by those skilled in the art, registering of images is a technique whereby images generated at different times, by different modalities, or from different positions, i.e., views, are conformed to one another so that one or more features depicted in the images are aligned. Registration may be performed based on markers or indicators placed intentionally within the images or based on identifiable structures or features within the unprocessed or processed image data. Other techniques for registration may also be used.

In one embodiment, registration may be used to align the structures present in a pair (or more) of projection images acquired at different energy levels at the same location or at slightly offset locations. For example, referring to FIG. 6, an exemplary process in accordance with this embodiment is depicted for registering multi-energy projection images. The exemplary process includes acquiring a first projection image based on X-rays having a first energy profile, as depicted at step 138, and a second projection image based on X-rays having a second energy profile, as depicted at step 140 at the same or a slightly offset location. Furthermore, as will be appreciated by those of ordinary skill in the art, additional projection image acquisitions may occur for additional X-ray energy profiles at the same or slightly offset locations, as depicted at step 142. If a determination is made at decision block 144 that the acquisition process is not complete, the X-ray source is activated at the next location, as depicted at step 146. If, however, the acquisition is determined to be complete at decision block 144, spatial registration may proceed for the acquired projection images.

The markers to be used for registration are identified in the images to be registered at step 148. Based on the identified markers, the images are registered or aligned at step 150 to generate registered projection images 152 may be processed, such as by reconstruction and/or reconstruction and decomposition, to generate one or more desired tomosynthesis images.

Figure 7:
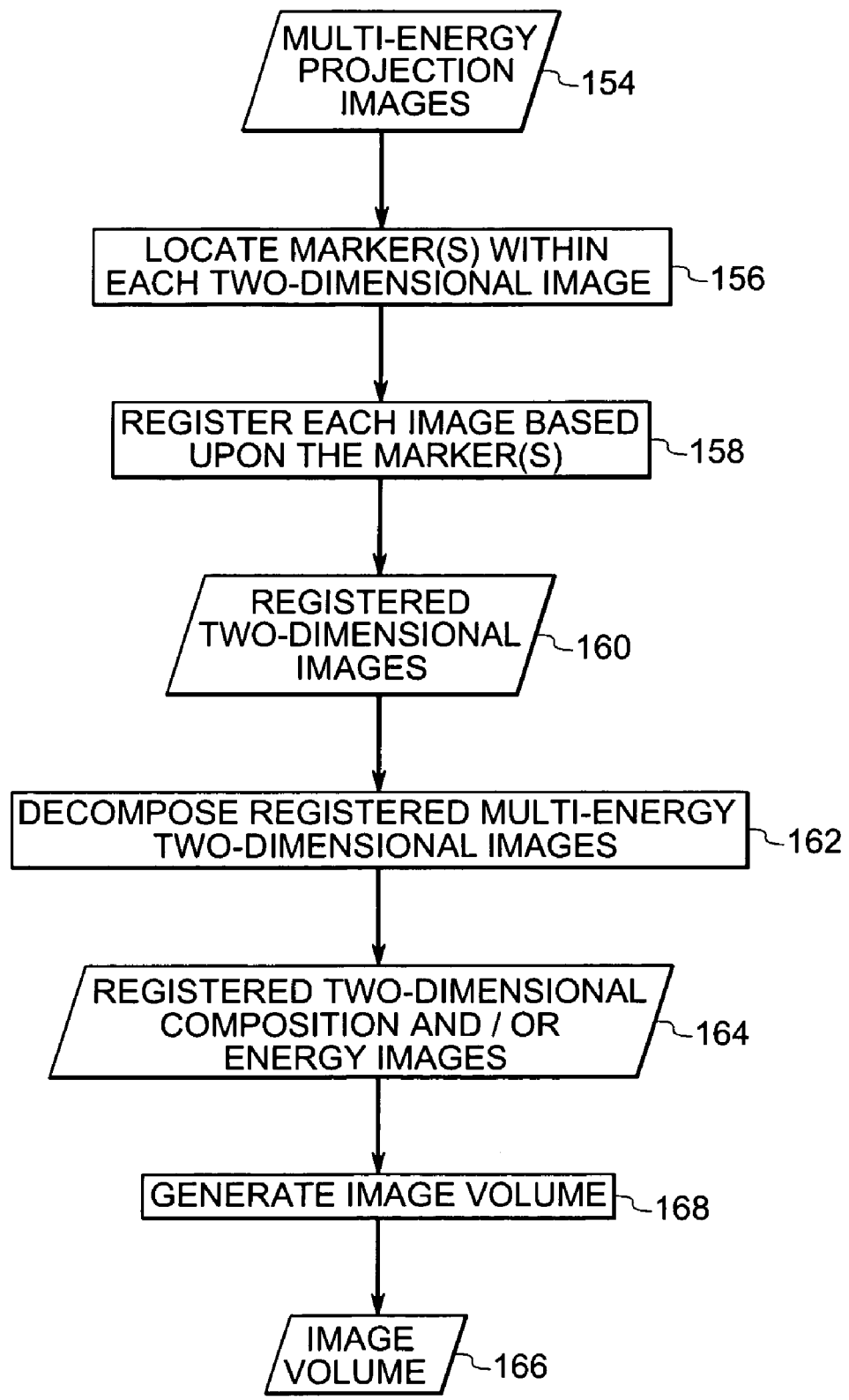
FIG. 7 is a flowchart illustrating exemplary process steps for registering reconstructed multi-energy tomosynthesis images in accordance with another embodiment of present technique.

In addition to registration of the projection images, other registration techniques may also be employed. For example, in one embodiment two-dimensional multi-energy images may be registered prior to display or visualization. For example, referring to FIG. 7, one technique for registering multi-energy images in accordance with an embodiment of the present technique is described. In particular, the depicted process may be useful in registering two-dimensional multi-energy images, which may then be combined to generate a three-dimensional or image volume. The exemplary process includes identifying registration markers in the two-dimensional images at step 156. The images are registered based on the identified markers at step 158 to generate registered two-dimensional images 160. The registered two-dimensional images 160 are decomposed at step 162 to generate registered two-dimensional composition and/or energy images 164. These registered two-dimensional images are then associated or combined to generate an image volume 166 at step 168.

Figure 8:
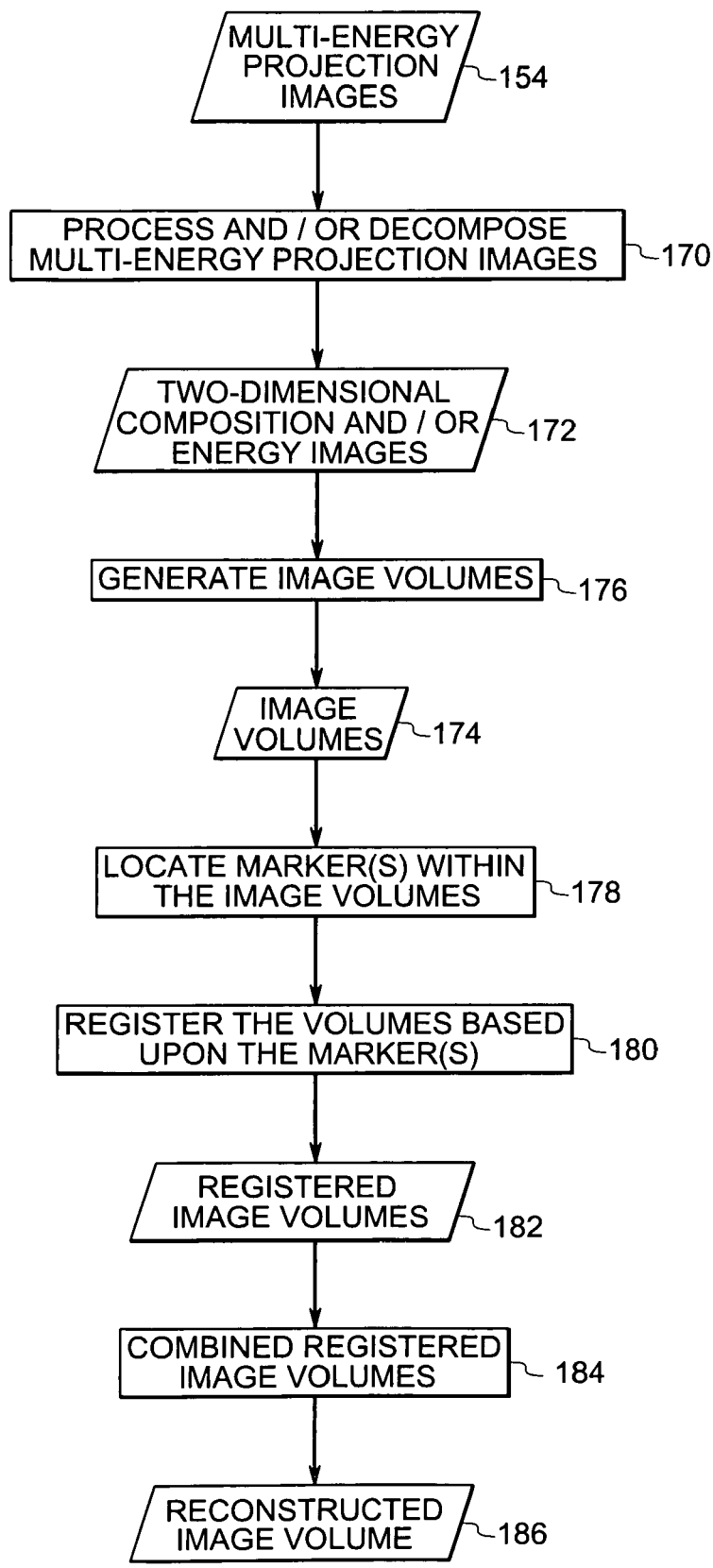
FIG. 8 is a flowchart illustrating exemplary process steps for registering reconstructed multi-energy tomosynthesis images in accordance with yet another embodiment of present technique.

Alternatively, in another embodiment, the registration process may be performed in the image volume, i.e., in three-dimensional space, as opposed to in two-dimensional space. For example, referring to FIG. 8 an exemplary process is depicted for registration of a volume in accordance with one embodiment of present technique. In this embodiment, the multi-energy projection images 154 are processed, with or without decomposition, at step 170 to generate two-dimensional composition and/or energy images 172. The processed two-dimensional images 172 are then used to generate image volumes 174 at step 176. In one example, a separate image volume 174 is generated for each processed two-dimensional image. Registration markers are identified within the image volumes 174 at step 178. The image volumes 174 are then registered based on the identified markers at step 180 to generate registered image volumes 182, which is aligned in all three-spatial dimensions. The registered image volumes 182 are then combined in a suitable way at step 184 to create a reconstructed image volume 186. In one embodiment, the combination at step 184 is accomplished by simple averaging, such as if no additional decomposition is to be performed. In another embodiment, the combination at step 184 includes an additional decomposition step in addition to the combination by simple or weighted averaging or by other combinatorial techniques.

Combinations of two-dimensional and three-dimensional registration techniques may also be employed. In one example, all images corresponding to the same X-ray emission location are registered using two-dimensional registration techniques, while data corresponding to different emission locations is registered in three-dimensions.

The preceding discussion relates generally to processing of multi-energy projection images to reduce variations due to temporal or spatial acquisition differences. In addition, in one embodiment of the present technique, one or more automated routines and/or algorithms may be applied to the acquired projection data, to the reconstructed energy tomosynthesis images, or to the reconstructed and decomposed composition tomosynthesis images. For example, referring now to FIG. 9, one or more computer-aided detection and/or diagnosis (CAD) may be applied to multi-energy projection images 52 at step 192 to generate a set of CAD results 194. As will be appreciated by those skilled in the art, the CAD results 194 may provide a diagnostic data that may be used to assist a diagnostician in detecting or diagnosing a structure or abnormality observed in the data or images. For example, the CAD results 194 may include the identification of one or more identified lesions, calcifications, or other structural abnormalities, a statistical likelihood of a diagnosis associated with an identified structure, a ranking of identified structures based on one or more severity criteria, or other detection and/or diagnoses designed to assist a diagnostician.

Similarly, in another embodiment, the CAD algorithms may be applied at step 192 to a set of energy and/or composition tomosynthesis images 190 reconstructed or reconstructed and decomposed from the multi-energy projection images 52 at step 188. In such an embodiment, the resulting CAD results 194 also provide detection and/or diagnosis information useful to a diagnostician, as described above. In both exemplary embodiments, the CAD results 194, may be displayed at step 196 (as discussed with regard to FIG. 1) in conjunction with the three-dimensional image(s) 190 to which they relate, such as by superimposing the CAD results 194 on the image(s) or by displaying visual markers, color-coding, or textual data derived from the CAD results 194. Furthermore, in another embodiment, the CAD results 194 may, automatically or via operator interaction, be used to perform additional, targeted image acquisitions, as depicted at step 198, of one or more regions of interest identified by the CAD results 194. The specified multi-energy projection images 200 generated by such a targeted acquisition may then be reconstructed or reconstructed and decomposed to generate a targeted energy and/or composition view of the region identified in the CAD results as warranting additional examination.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A multi-energy tomosynthesis imaging system, the system comprising:
   an X-ray source configured to emit X-rays at a plurality of locations within a limited angular range relative to an imaging volume;
   a digital detector comprising an array of detector elements, wherein the digital detector is configured to generate a plurality of images in response to the emitted X-rays;
   detector acquisition circuitry configured to acquire the plurality of images from the digital detector; and
   processing circuitry configured to decompose the plurality of images based on energy characteristics and to reconstruct the plurality of images to generate a three-dimensional multi-energy tomosynthesis image.

2. The system of claim 1, wherein the processing circuitry decomposes the plurality of images prior to reconstructing the plurality of images.

3. The system of claim 1, wherein the processing circuitry reconstructs the plurality of images prior to decomposing the plurality of images.

4. The system of claim 1, comprising an operator workstation configured to display the three-dimensional image.

5. The system of claim 1, wherein the X-ray source comprises an X-ray tube configured to be moved to each of the plurality of locations.

6. The system of claim 1, wherein the X-ray source comprises a respective X-ray tube at each of the respective plurality of locations.

7. The system of claim 1, wherein the X-ray source comprises a plurality of X-ray tubes, wherein each X-ray tube of the plurality of X-ray tubes may be positioned at least one of the plurality of locations.

8. The system of claim 1, wherein the X-ray source comprises a solid-state X-ray emitter configured to be moved to each of the plurality of locations.

9. The system of claim 1, wherein the X-ray source comprises a respective solid-state X-ray emitter at each of the respective plurality of locations.

10. The system of claim 1, wherein the X-ray source comprises a plurality of solid-state X-ray emitters, wherein each solid-state X-ray emitter of the plurality of solid-state X-ray emitters may be positioned at least one of the plurality of locations.

11. The system of claim 1, wherein the digital detector comprises a non-energy discriminating detector.

12. The system of claim 11, further comprising a filter configured to filter X-rays at different energy levels.

13. The system of claim 12, wherein the filter comprises at least one of copper, aluminum, iron, molybdenum, tin, barium, gadolinium, tungsten, or lead.

14. The system of claim 1, wherein the digital detector comprises an energy discriminating detector.

15. The system of claim 1, wherein the digital detector generates digital signals in response to the emitted X-rays.

16. The system of claim 1, further comprising a sensing device to monitor motion of a patient or motion of one or more organs of a patient.

17. The system of claim 16, wherein the sensing device comprises at least one of a cardiac motion sensor or a respiratory motion sensor.

18. The system of claim 16, wherein the sensing device measures at least one of an electrical activity, a displacement, an acceleration, a strain, a velocity, a pressure, or a sound.

19. The system of claim 1, wherein the three-dimensional image comprises a quantitative image.

20. The system of claim 1, wherein the three-dimensional image comprises at least one of a low-energy tomosynthesis image, an intermediate-energy tomosynthesis image, a high-energy tomosynthesis image, a soft-tissue tomosynthesis image, a bone-tomosynthesis image or a contrast medium tomosynthesis image.

21. The system of claim 1, further comprising an anti-scatter grid disposed proximal to the digital detector and configured to reduce an incidence of scattered X-rays on the digital detector.

* * * * *

UNITED STATES PATENT AND TRADEMARK OFFICE
CERTIFICATE OF CORRECTION

PATENT NO. : 7,440,603 B2
APPLICATION NO. : 12/037730
DATED : October 21, 2008
INVENTOR(S) : Eberhard et al.

It is certified that error appears in the above-identified patent and that said Letters Patent is hereby corrected as shown below:

In the Drawings: In Fig. 4, Sheet 4 of 9, for Tag "122", Line 2, delete "COPLETE ?" and insert -- COMPLETE ? --, therefor.

Figure 6:
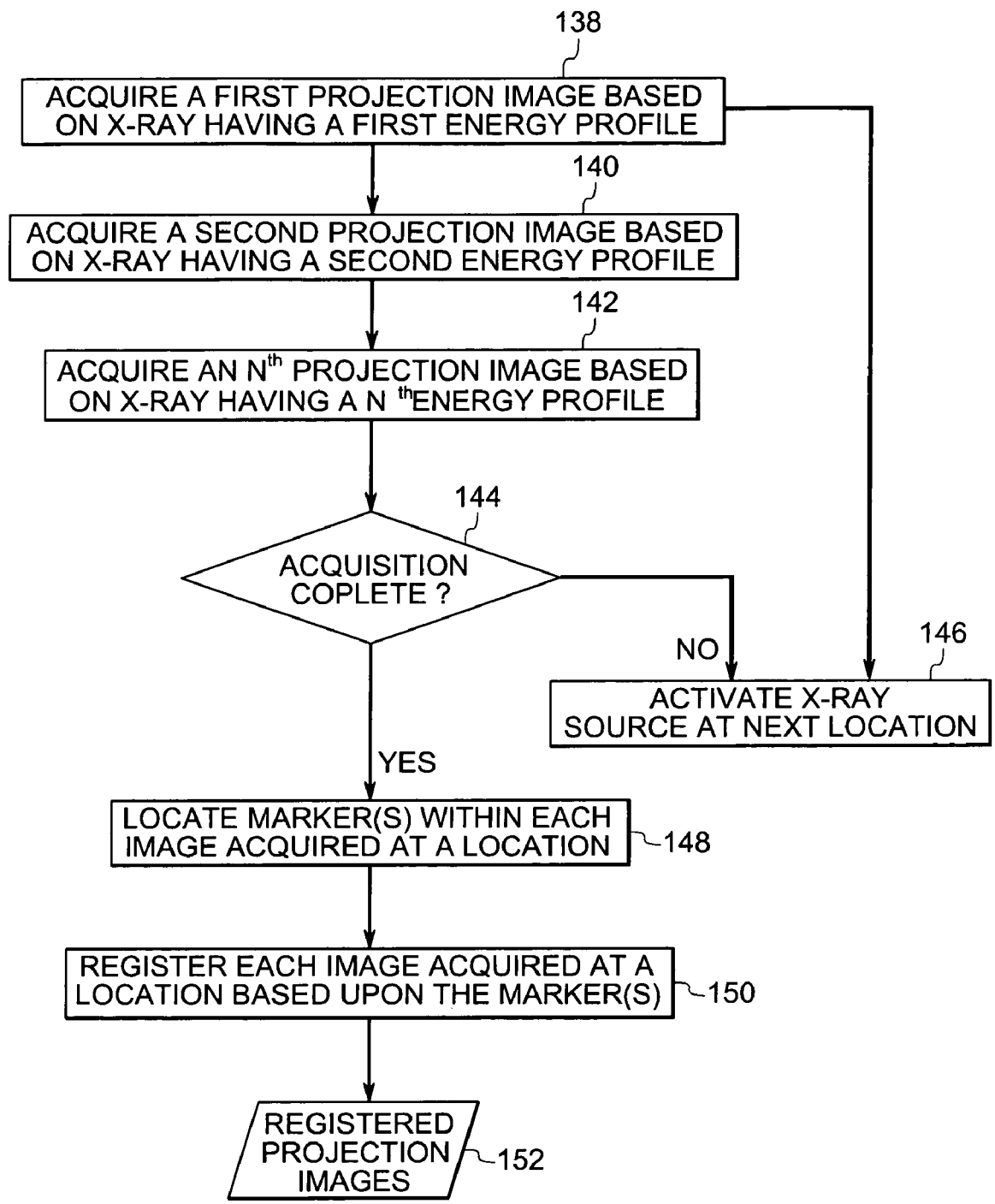
FIG. 6 is a flowchart illustrating exemplary process steps for registering multi-energy projection images in accordance with aspects of present technique.

In the Drawings: In Fig. 6, Sheet 6 of 9, for Tag "142", Line 2, delete "N $^{th}$ENERGY" and insert -- N$^{th}$ ENERGY --, therefor.

In the Drawings: In Fig. 6, Sheet 6 of 9, for Tag "144", Line 2, delete "COPLETE ?" and insert -- COMPLETE ? --, therefor.

Figure 9:
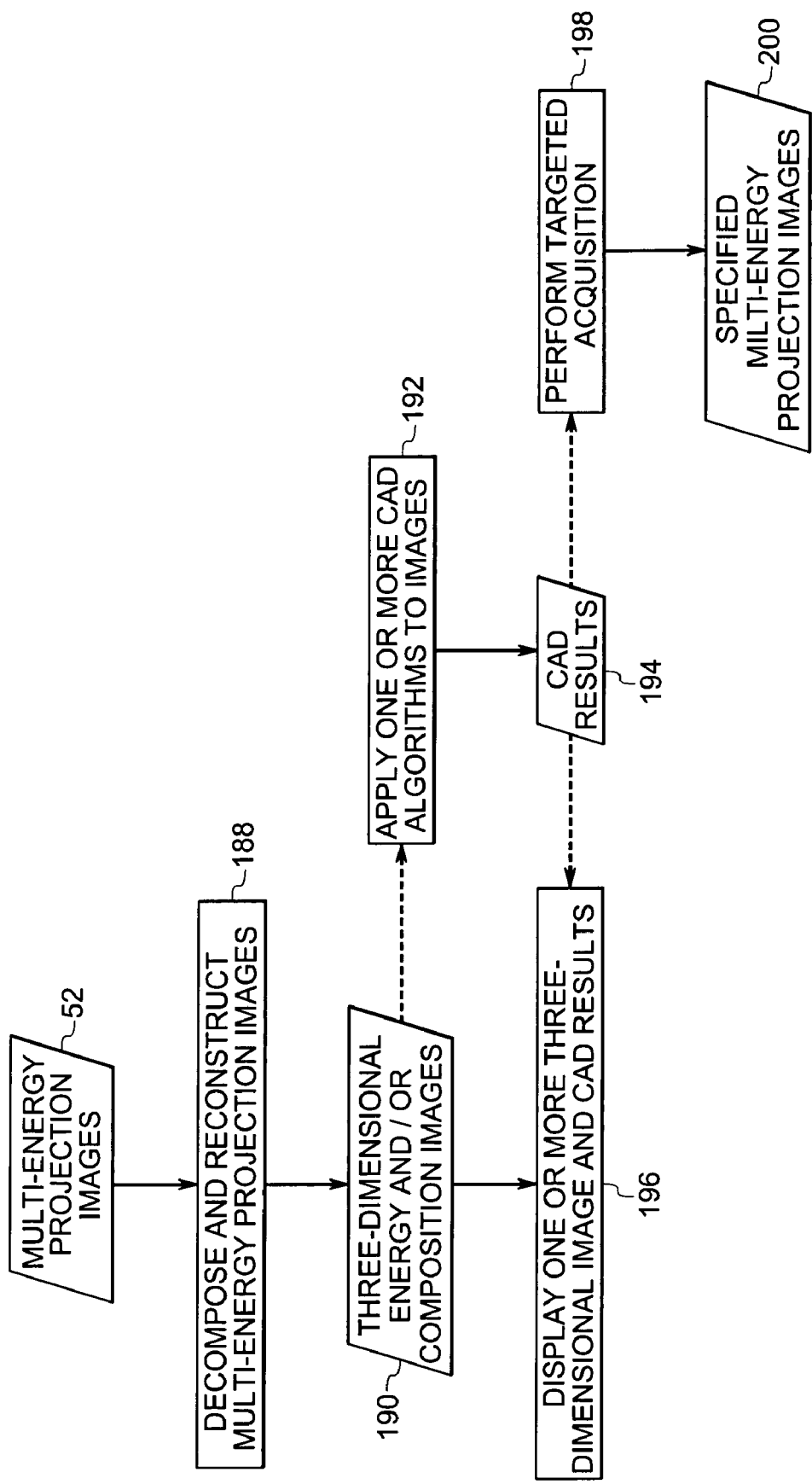
FIG. 9 is a flowchart illustrating exemplary process steps for computer-aided diagnosis (CAD) using multi-energy tomosynthesis images in accordance with aspects of present technique.

In the Drawings: In Fig. 9, Sheet 9 of 9, for Tag "200", Line 2, delete "MILTI-ENERGY" and insert -- MULTI-ENERGY --, therefor.

In Column 12, Line 11, in Claim 7, after "positioned" insert -- at --.

In Column 12, Line 22, in Claim 10, after "positioned" insert -- at --.

Signed and Sealed this

Eighteenth Day of August, 2009

David J. Kappos
*Director of the United States Patent and Trademark Office*